(12) United States Patent
Vega Galvez et al.

(10) Patent No.: US 12,141,089 B2
(45) Date of Patent: Nov. 12, 2024

(54) DATA MANIPULATION USING INTRAORAL CONNECTED DEVICES

(71) Applicant: Augmental Technologies Inc., San Francisco, CA (US)

(72) Inventors: Tomas Alfonso Vega Galvez, San Francisco, CA (US); Corten Singer, San Francisco, CA (US); Carlos Nunez Lopez, Arlington, MA (US)

(73) Assignee: Augmental Technologies Inc., San Francisco, CA (US)

( * ) Notice: Subject to any disclaimer, the term of this patent is extended or adjusted under 35 U.S.C. 154(b) by 288 days.

(21) Appl. No.: 17/696,931

(22) Filed: Mar. 17, 2022

(65) Prior Publication Data

US 2022/0206986 A1 Jun. 30, 2022

Related U.S. Application Data

(63) Continuation-in-part of application No. 17/366,186, filed on Jul. 2, 2021.

(60) Provisional application No. 63/301,501, filed on Jan. 21, 2022, provisional application No. 63/162,444, filed on Mar. 17, 2021, provisional application No. 63/063,455, filed on Aug. 10, 2020, provisional application No. 63/047,946, filed on Jul. 3, 2020.

(51) Int. Cl.
*G06F 13/40* (2006.01)
*G06F 13/42* (2006.01)

(52) U.S. Cl.
CPC ...... *G06F 13/4068* (2013.01); *G06F 13/4282* (2013.01); *G06F 2213/0016* (2013.01)

(58) Field of Classification Search
CPC ............ G06F 13/4068; G06F 13/4282; G06F 2213/0016
See application file for complete search history.

(56) References Cited

U.S. PATENT DOCUMENTS

| | | |
|---|---|---|
| 8,812,096 B2 | 8/2014 | Flaherty et al. |
| 10,137,363 B2 | 11/2018 | Parshionikar |
| 10,234,938 B2 | 3/2019 | Moffat et al. |
| 10,542,929 B2 | 1/2020 | Kimmel |
| 10,600,417 B2 | 3/2020 | Tormasov et al. |
| 2016/0117940 A1 | 4/2016 | Gomory et al. |
| 2016/0154468 A1* | 6/2016 | Kimmel ............... A61C 8/0093 345/156 |
| 2016/0367188 A1 | 12/2016 | Malik et al. |

(Continued)

*Primary Examiner* — Robert J Michaud
(74) *Attorney, Agent, or Firm* — Adams Intellex, PLC

(57) ABSTRACT

Data manipulation using intraoral, connected devices is disclosed. Wired connectivity is provided between a first device and a second device, both inside the mouth. The first device comprises a processor device. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth. Wireless connectivity is provided between the first device and a device outside the mouth. The wireless connectivity is enabled using a wireless transceiver. Data transmission is enabled between the first device and the device outside the mouth. The enabling includes powering at least the first device using an intraoral energy source.

23 Claims, 8 Drawing Sheets

(56) References Cited

U.S. PATENT DOCUMENTS

| | | |
|---|---|---|
| 2018/0300008 A1 | 10/2018 | Rasanen |
| 2019/0004596 A1 | 1/2019 | Postal et al. |
| 2019/0302894 A1 | 10/2019 | Alvarado et al. |
| 2021/0085247 A1 | 3/2021 | Meirav |
| 2021/0256246 A1* | 8/2021 | Dagdeviren ......... G06V 40/172 |
| 2021/0282953 A1* | 9/2021 | Sakuma ............. H03F 3/45475 |

* cited by examiner

DATA MANIPULATION USING INTRAORAL CONNECTED DEVICES

RELATED APPLICATIONS

This application claims the benefit of U.S. provisional patent applications "Intraoral Connected Processing Devices" Ser. No. 63/162,444, filed Mar. 17, 2021 and "Intraoral Electronic Sensing for Health Monitoring" Ser. No. 63/301,501, filed Jan. 21, 2022.

This application is also a continuation-in-part of U.S. patent application "Data Manipulation Using Remote Augmented Sensing" Ser. No. 17/366,186, filed Jul. 2, 2021, which claims the benefit of U.S. provisional patent applications "Data Manipulation Using Remote Augmented Sensing" Ser. No. 63/047,946, filed Jul. 3, 2020, "Gestural Sensing Using In-Ear Inertial Measurements" Ser. No. 63/063,455, filed Aug. 10, 2020, and "Intraoral Connected Processing Devices" Ser. No. 63/162,444, filed Mar. 17, 2021.

Each of the foregoing applications is hereby incorporated by reference in its entirety.

FIELD OF ART

This application relates generally to data manipulation and more particularly to data manipulation using intraoral connected devices.

BACKGROUND

The variety of electronic devices or "gadgets" that is available today is simply dizzying. Further, the people who use those electronic devices are passionate about them. With a few possible exceptions, people are rarely far from their favorite gadgets. The gadgets are designed and used for communicating; performing work-related tasks such as drafting documents, spreadsheets, and presentations; engaging in educational tasks such as classes, tutorials, recitations, and laboratories; performing research tasks such as data collection and analysis; processing data for governmental or business intelligence; supporting facilities operations; and much more. The electronic devices can range from desktop computers and laptop computers to tablet computers; to smartphones and PDAs; to storage devices, input devices, and output devices; and others. Other devices are designed for diversion, entertainment, and generally, for fun. These latter electronic devices include game consoles, portable gaming devices, and music players. While these devices all include often powerful computational capabilities, their designs have been fine tuned for specific capabilities including graphics rendering speed and image resolution, processing speed, and audio fidelity. While some of the electronic devices are intended to reside in offices or laboratories, many are designed to be conveniently portable. These portable devices can easily be slipped into a briefcase, messenger bag, or backpack, while others easily fit into pockets or can even be clipped to clothing. The devices provide information, videos, and music, and can ease the tedium of routine tasks such as commuting. Whatever the intention, use, or purpose, there are electronic devices available to meet it.

The electronic devices are commonly used for consuming a wide variety of online content. The content can include politics, news updates, sports scores, and other items of importance, interest, amusement, and diversion. The content can be informational, educational, useful, silly, and age-appropriate, or not. Other electronic device uses include keeping in touch with family, friends, coworkers, and other people through email, chat, social media, photos, and even telephony. The ways a user employs an electronic device to consume media or engage with others depend on the particular device. Smartphones are delightfully portable, enabling usage while a person is out and about. A smartphone can access the Internet; connect to news, information, and social media sites; enable online shopping; and support email, chatting, and calls; among myriad other uses. One disadvantage of the smartphone is that the smartphone display screen is relatively small. A tablet device offers much of the portability of the smartphone with the key advantage of a larger display. The larger display makes interactions with others more enjoyable and greatly enhances media streaming. A laptop device is less portable than the smartphone or the tablet, but provides a larger display. The laptop can access the Internet, interact with others, and engage in many other popular uses. The laptop offers the distinct advantage in that its more powerful processors are better suited to more complex uses such as creative activities, learning, and working.

SUMMARY

The use of personal and other electronic devices has become practically ubiquitous. These devices are used for purposes including commerce, education, research, records processing, and entertainment, among many, many others. A variety of techniques have been developed that enable users to interact with their devices. The interaction techniques often include the use of components such as keyboards of varying types, mice, trackpads, graphics drawing tablets, touch screens, and smart pens or pencils. Some of these interaction components are particularly well adapted for desktop use such as keyboards, mice, trackpads, and graphics tablets. These components can be installed, configured, and left in place for a user to access when they need the interaction components. Smaller and lightweight versions of these interaction components often can be developed and used "on the go", such as small form-factor or folding keyboards, wireless mice and trackpads, etc. Additional interaction components such as touch screens, smart pens, and text to speech applications are also useful. While these interaction components are highly developed and widely used, they are designed to be used while the user is focused on and engaging with their electronic device. While this interaction model can be acceptable for office workers, students, retail employees, and others who can sit or stand at a desk, or easily interact with a terminal such as a point-of-sale terminal, the model fails to enable human-computer interactions during many other common activities.

People engage in activities that require them to interact with a wide variety of electronic devices while they are performing other tasks. These often-divergent activities can include accessing a repair manual while working on a piece of equipment, interacting with a digital recipe while cooking, reading instructions while operating a machine, or even using augmented reality while performing surgery. Another common scenario is that while engaging in a video call, actions such as opening a file or initiating a computer search for an answer to a question that came up during the call are necessitated. Viewing, talking, typing, mousing, swiping, and similar activities all contribute to enabling and enhancing the user experience. Situations exist, however, in which a person cannot use conventional input/output techniques. In such situations, overt interaction by a user with an electronic device is socially unacceptable, impossible, dangerous, or even illegal, such as using a handheld device while operating a vehicle. In the legal latter situations, people are performing other tasks that demand their attention and concentration while simultaneously wanting or needing to interact with an electronic device. The tasks can engage the user's hands, the user may have physical challenges or limitations which prevent human-machine interaction, or the situations include low light conditions, limited access to input/output devices, or even covert activities.

Intraoral, connected devices enable data manipulation. Wired connectivity is provided between a first device inside a mouth and a second device inside the mouth. The first device comprises a processor device, and the second device comprises an intraoral sensing device. The wired connectivity is provided by a serpentine coupling. The serpentine coupling comprises an electrical cable. The serpentine coupling enables three-dimensional flexibility inside the mouth for the coupling. The serpentine coupling enables three-dimensional overlap of the electrical cable within the mouth, and the three-dimensional overlap provides conformal routing over a surface of the mouth. Wireless connectivity is provided between the first device and a device outside the mouth, where the wireless connectivity is enabled using a wireless transceiver. Data transmission is enabled between the first device and the device outside the mouth. The enabling includes powering at least the first device using an intraoral energy source, where the intraoral energy source comprises a battery, a capacitor, or an inductive field device.

A processor-implemented method for data manipulation is disclosed comprising: providing wired connectivity between a first device inside a mouth and a second device inside the mouth, wherein the wired connectivity is provided by a serpentine coupling, and wherein the serpentine coupling enables three-dimensional flexibility inside the mouth for the coupling; providing wireless connectivity between the first device and a device outside the mouth, wherein the wireless connectivity is enabled using a wireless transceiver; and enabling data transmission between the first device and the device outside the mouth. In embodiments, the enabling includes powering at least the first device using an intraoral energy source. In embodiments, the serpentine coupling comprises an electrical cable. In embodiments, the serpentine coupling enables three-dimensional overlap of the electrical cable within the mouth. And in embodiments, the three-dimensional overlap provides conformal routing over a surface of the mouth.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
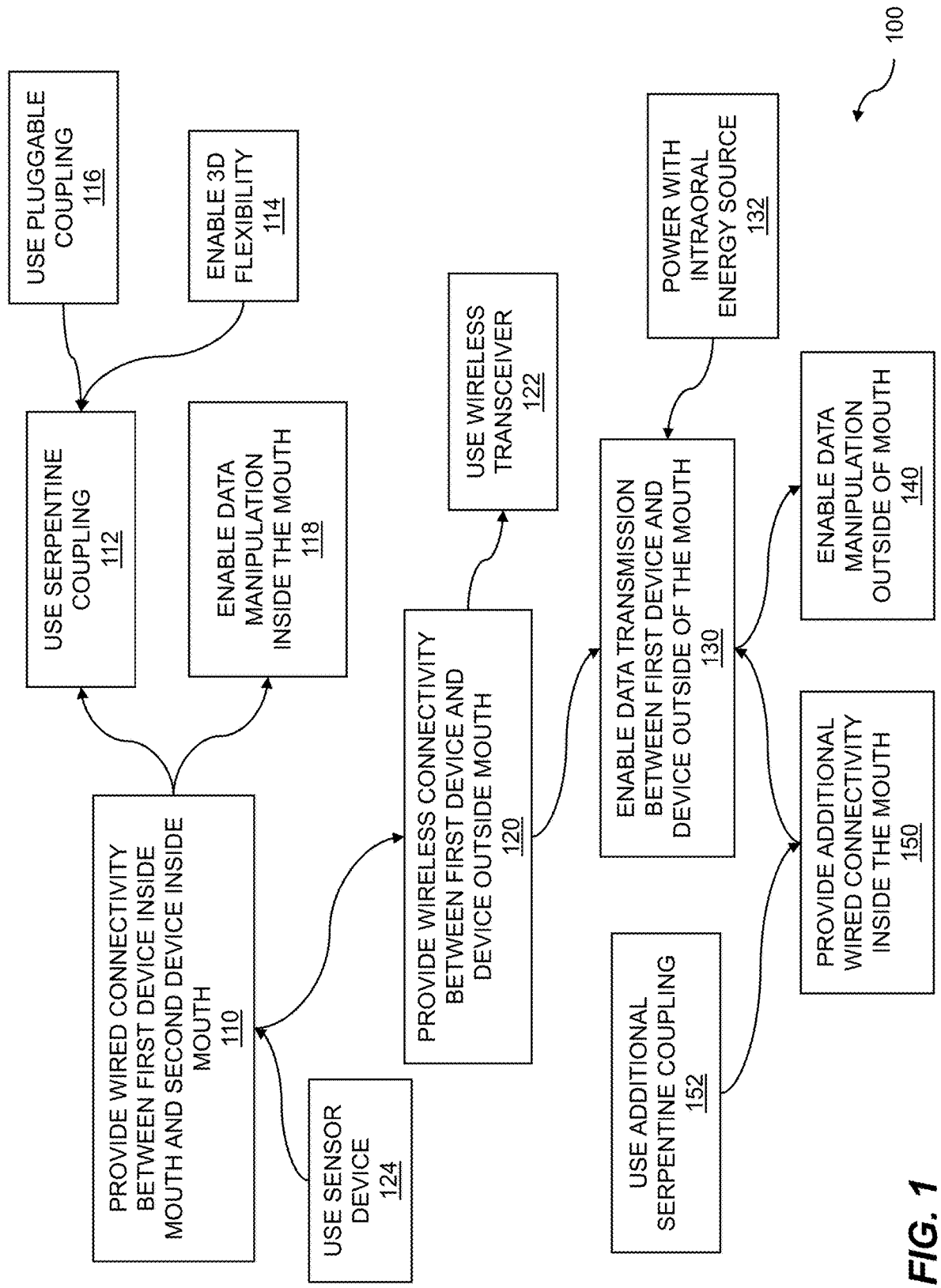
FIG. 1 is a flow diagram for intraoral, connected devices.

This disclosure provides techniques for data manipulation using intraoral, connected devices. Users employ a diversity of techniques to interact with processors of various descriptions. The processors can include personal electronic devices such as smartphones, tablets, and personal digital assistants (PDAs); laptop and desktop computers; servers, whether local or cloud-based; and so on. The techniques by which users interact with processors can be based on typing on a keyboard, moving and clicking a mouse, swiping and tapping or pressing a trackpad, speaking into a microphone, reading contents of a display, and so on. However, use of these typical input/output techniques for user-processor interaction is not always possible. One or more impairments can be associated with a particular user. Motor impairments can prevent a user from typing and controlling a mouse or trackpad, visual impairments can prevent a user from reading a display, and so on. Other impairments can include situational impairments. A situational impairment, which can impede or prevent a user from employing common input/output techniques, is based on a user's situation. A situational impairment can include a bright light environment in which a user cannot read a display, a low light situation preventing use of a keyboard, and the like. Situational impairments can also be based on circumstances of the user for which speaking violates rules or social mores, accessing a screen is deemed rude, and the like. Further situations can include the user being engaged in another activity such as machine operation or surgery. In these latter cases, the user is unable to access a keyboard, mouse, or trackpad because the user's hands are otherwise occupied.

In disclosed techniques, data manipulation uses intraorally connected devices. The devices can include processing devices and sensor devices. The sensor devices can provide data to, or receive data from, processing devices. The processing devices can include wireless connectivity enablement. Data is transmitted, or communicated, from a first device included in a mouth to a second device within the mouth. The transmitting is accomplished through a serpentine coupling. The transmitting can be electrically based in the coupling. The serpentine coupling can include one or more conductors. The one or more conductors can be insulated within the coupling, both from each other and from any external connections. The serpentine coupling can include other forms of data transmission, such as light, or optical, data transmission. Wireless connectivity is provided between the first device and a device outside the mouth. The wireless connectivity that is provided uses a wireless transmitting device. For example, a wireless transmitting device can be coupled to an oral sensing interface through the serpentine coupling. A tongue position sensor (TPS) can be coupled to a processing device, which can include wireless transmitting capabilities. Inertial measurement units (IMUs) can be coupled to the first device. The IMUs can be attached to non-adjacent locations of the oral sensing interface. Data manipulation can be enabled within the processor. The enabling can be based on the wireless connectivity and output from a TPS and an IMU. Feedback in the form of both haptic feedback and audio feedback can be provided to the interface user. In embodiments, the first device or the second device can comprise a digital sensor, an analog sensor, a battery coupled to circuitry, or other circuit implementations.

FIG. 1 is a flow diagram for intraoral, connected devices. The connected devices can collect, generate, process, or transmit data. The data can be obtained from sensors, including augmented sensors, smart sensors, passive sensors, active sensors, and so on, where the sensors can be located within a mouth of a user. In but one usage example, a user, who can be experiencing situational impairment, may operate various sensors to enable data manipulation in a processor. Situational impairment can refer to a user's inability to interact with a computer, processor, handheld device, and so on, due to a situation in which the user finds himself. The flow 100 includes providing wired connectivity between a first device inside a mouth and a second device inside the mouth 110. The devices can include processors, sensors, smart sensors, and so on. A processing device can be used to control one or more sensors, collect data from the sensors, translate or scale the data from the sensors, communicate wirelessly with other devices, etc. The processing device can prepare sensor data for transmission, processing, and the like. The wired connectivity inside the mouth can enable data manipulation inside the mouth 118, discussed more later.

In the flow 100, the communicating is accomplished through a serpentine coupling 112. The serpentine coupling can comprise one or more conductors. In embodiments, the serpentine coupling can include a serpentine wire. The wire can include a round wire, a flat wire, and so on. The serpentine wire can resemble a "wave train". The resemblance of the serpentine wire wave train can be based on forming the serpentine wire to resemble curved waves such as sine waves, flat-topped waves such as square waves, and so on. In embodiments, the serpentine wire can have a varying serpentine amplitude. That is, the amplitude or excursion of a particular wave can vary over the length of the serpentine wire. The serpentine wire can also have substantially constant amplitude over the length of the serpentine wire. In other embodiments, the serpentine wire can have a varying serpentine period. The varying serpentine period can be associated with changes in distance between the peak of one serpentine wire wave and the peak of the next serpentine wire. The changes in period can be used to enable the serpentine wire to travel over, around, or between features found within a mouth. The serpentine coupling can comprise a pluggable coupling 116. A pluggable coupling can have one or both ends of the coupling terminated in a small form-factor plug, such that the plug mates with a receptacle to complete an electrical connection. The pluggable couplings enable various predefined sizes and shapes of serpentine couplings to be modularly available for embedding in a custom-formed intraoral retainer or other formfitting structure as will be described later. The serpentine coupling enables three-dimensional (3D) flexibility 114 of the coupling. The coupling can bend, twist, and flex in multiple directions to facilitate placement over, through, and around a mouth. In embodiments, the serpentine coupling enables three-dimensional overlap of the electrical cable within the mouth. In embodiments, the three-dimensional overlap provides conformal routing over a surface of the mouth.

In embodiments, the serpentine wire can be routed in the "valley" space between teeth. While there is not generally a large space between adjacent teeth, there is generally a small valley formed by the receding edges of a tooth's top or bottom surface. Because normal occlusion of the upper and lower teeth of a mouth could damage a serpentine coupling traversing the incising or masticating surfaces of occluding teeth, routing through a valley space can be useful. In embodiments, the serpentine coupling is routed in the valley space between teeth of the mouth. Placing the serpentine wire between teeth can enable easy placement of the first and the second devices, additional devices, and so on. In further embodiments, the serpentine wire can travel behind a last molar tooth. Depending on the sizes and shapes of teeth, the relative position of the gum line to the top of the last molar, and so on, placing the serpentine wire behind the last molar can provide a convenient and comfortable location for the wire. In other embodiments, the serpentine wire travels over one or more teeth, but only when occlusal damage is not a concern, such as when a tooth is missing its mating tooth above or below. In some usage cases, placing the serpentine wire over the one or more teeth can enable shorter serpentine wires, more convenient placement of the first and second processing devices, etc.

The flow 100 includes providing wireless connectivity 120 between the first device and a device outside the mouth. The device outside the mouth can include a computing device, a personal electronic device, and so on. The device outside the mouth can include a desktop computer, a laptop computer, a smartphone, tablet, or PDA, and so on. In the flow 100, the wireless connectivity is accomplished using a wireless transceiver 122. The wireless connectivity can be based on communications standards, preferred protocols, low power techniques, and so on. The wireless connectivity can be based on the 802.11 family or "Wi-Fi™", Bluetooth™, Zigbee™, and so on. The wireless connectivity can be based on near field communication (NFC). The wireless connectivity can be based on near field magnetic induction (NFMI). The wireless connectivity can be provided as part of a wireless personal area network (WPAN). The flow 100 further includes using a sensor device 124 as one of the devices inside the mouth. Various sensor devices can be used. One such device can be a tongue position sensor (TPS), which can be coupled to the first device. The TPS can be used to detect a three-dimensional position of a tongue within a mouth, pressure exerted by a user's tongue, and so on. In embodiments, the first processing device can include the TPS. In further embodiments, the TPS comprises an oral sensing interface. An oral sensing interface can be worn by a user, placed within the user's oral cavity, and so on. In embodiments, the oral sensing interface can include a retainer or "bite plate". The retainer can be custom fitted to the user in order to enable both proper fit of the interface and comfort of the user. The tongue position sensor can be located such that it can be easily accessible to the tongue. In embodiments, the TPS can be placed below the tongue of the user, such as when a retainer is worn on the lower teeth. An alternative location for the TPS can be above the tongue, such as when the retainer is worn on the upper teeth. The TPS can include electrodes, pressure sensors, etc.

Other sensors, smart sensors, and so on can be coupled to the first processing device. The coupling can be accomplished using the serpentine couplings. Embodiments include coupling at least one inertial measurement unit (IMU) to the first device. The IMU(s) can be used to determine position, movement, acceleration, and so on. In embodiments, at least two inertial measurement units are located in nonadjacent locations within the mouth. An example placement of the IMUs is discussed below, where the IMUS are located to the left and the right of the retainer. The at least two IMUs can be used to detect tongue or jaw positions, rotation, acceleration, and so on. In further embodiments, the second processing device can comprise a first inertial measurement unit, where the first processing device is adjacent to the palate of the mouth. The first inertial measurement unit can be placed at various positions within the mouth. In embodiments, the second processing device is located outside of teeth within the mouth. The positioning of the second processing device can be determined based on efficacy, comfort, convenience, and so on. In embodiments, the second processing device can be adjacent to a gumline of the mouth.

The flow 100 further includes enabling data transmission between the first device and the device outside of the mouth 130. The data transmission can involve data from the first or second devices, such as data manipulation input from a TPS or changes in pressure from a barometric sensor. Such data can be communicated to the device outside the mouth to enable data manipulation for a wide variety of purposes. The data manipulation can include opening, executing, and closing applications; accessing files for reading and writing; and so on. The enabling data manipulation can be based on opening and closing windows, providing data and other inputs to the processor, receiving results or other communications from the processor, and so on. The data manipulation in the processor can enable a diversity of applications, assistive technologies, immersive technologies, and the like. In embodiments, the TPS can enable oral mouse function control. Mouse function control can include moving a cursor, clicking, and so on. In embodiments, the oral mouse function control includes mouse function detection, such as mouse movement, mouse swipes, mouse clicks, mouse double-clicks, and mouse wheel control. Further mouse functions, such as secondary functions, can be based on an amount of pressure exerted by the tongue on the TPS. In embodiments, the data manipulation can be targeted for one or more Internet of Things (IoT) devices. Such data manipulation can potentially enable control of any Internet-connected device using remote augmented sensing, and in particular, oral remote augmented sensing.

The flow 100 includes providing additional wired connectivity inside the mouth 150. Additional devices within the mouth can be coupled to the first device and/or to the device outside the mouth. The additional devices can be coupled to the first device using additional serpentine coupling 152. An additional or third device can include a wireless transmitting device, a battery, a battery charging device, and the like. The flow 100 can include powering the intraoral electronics described herein using an intraoral energy source 132. The intraoral energy source can include batteries, capacitors, and other energy storage and/or energy transformation devices, such as an inductive field device. In embodiments, the enabling includes powering at least the first device using an intraoral energy source. In embodiments, the intraoral energy source comprises a battery, a capacitor, or an inductive field device.

The flow 100 further includes enabling data manipulation outside of the mouth 140. The data manipulation can be controlled by a user, wherein the user is associated with the mouth, in response to active oral manipulation by the user of an oral sensing interface that comprises the first device and the second device. The data manipulation by the user can be based on user manipulating the TPS, the IMUs, or other sensors and smart sensors within the mouth. In embodiments, the active oral manipulation accomplishes data manipulation in the device outside the mouth. Discussed previously and throughout, data manipulation can include opening and closing files; opening, repositioning, and closing windows; and so on. The manipulation can emulate mouse or trackpad manipulation. In further embodiments, the oral manipulation assists in a situational impairment, which includes operating a machine. The impairments can include visual, motor, and cognitive impairments. In embodiments, the TPS and the at least two IMUs can be used to accommodate severe motor impairment in a person, which can limit or prevent the person from accessing a processor using conventional devices such as keyboards, mice, trackpads, monitors, and so on. Different from visual, motor, or cognitive impairments, situational impairments occur when a user is not able to use processors and devices because of their situation. Such situations can occur due to ambient conditions such as too much light to read a screen or too little light to use a keyboard or trackpad; too loud an environment to hear audio feedback from the processor or computing device; too little ambient noise where speaking would disturb others such as in a library or at a movie; etc. Other causes of situational impairment can include an inability to use standard input/output devices when socially unacceptable; when a user's hands, eyes, and voice are otherwise occupied; and when covert interaction with a processor is required. Some situational impairments can be associated with a particular user due to their physiological, mental, or emotional situation. For example, motor impairments can prevent a user from typing and controlling a mouse or trackpad, visual impairments can prevent a user from reading a display, and so on. In embodiments, the situational impairment accommodation can enable control of a joystick functionality without having to engage hand motor skills to control it traditionally. Examples can include operating a wheelchair or controlling another vehicle type.

Embodiments include providing feedback to a user of the interface. The feedback that is provided to the user of the interface can include results of data manipulation enabled in the processor, alerts, warnings, codes, and so on. In embodiments, the feedback can include haptic feedback generated by a haptic device attached to the interface. The haptic feedback can include vibration, pressure, a tingling sensation, and the like. In other embodiments, the feedback can include audio feedback generated by a sound generating device attached to the interface. The sound generating device can include a speaker, a transducer, and so on. In embodiments, the sound generating device can use jawbone structure for audio propagation.

Continuing with feedback, in embodiments, the feedback can originate in the processor and can be transmitted to the interface using the wireless connectivity. The wireless connectivity can be based on the various wireless techniques discussed throughout. In other embodiments, the feedback can originate in the processor and can be based on output previously received by the processor over a connection using the wireless connectivity. The output previously received by the processor can include TPS data, IMU data, data from other sensors that can be coupled to the interface, and the like. The feedback can be based on an action taken by the user. In embodiments, the feedback can be responsive to active oral manipulation by a user of the interface. The active oral manipulation can include the user moving their tongue to move the cursor, click, etc. In embodiments, the active oral manipulation can accomplish data manipulation in the processor. The active oral manipulation can access files for input and output, operate applications, and so on. In further embodiments, the feedback can be responsive to passive monitoring of a person using the interface. The passive monitoring can include monitoring the user's health, habits, activities, etc. In embodiments, the feedback can be used to control bruxism in the user. Bruxism, or "teeth grinding", can be quite harmful to the teeth. In other embodiments, the feedback can be used to control sleep apnea in the user. Sleep apnea can result from the airway closing off while sleeping. Sleep apnea can manifest as loud snoring, gasping, and so on, and has many undesirable side effects which can include headaches, depression, stroke, or heart failure. Various embodiments of the flow 100 can be included in a computer program product embodied in a non-transitory computer readable medium that includes code executable by one or more processors.

Figure 2:
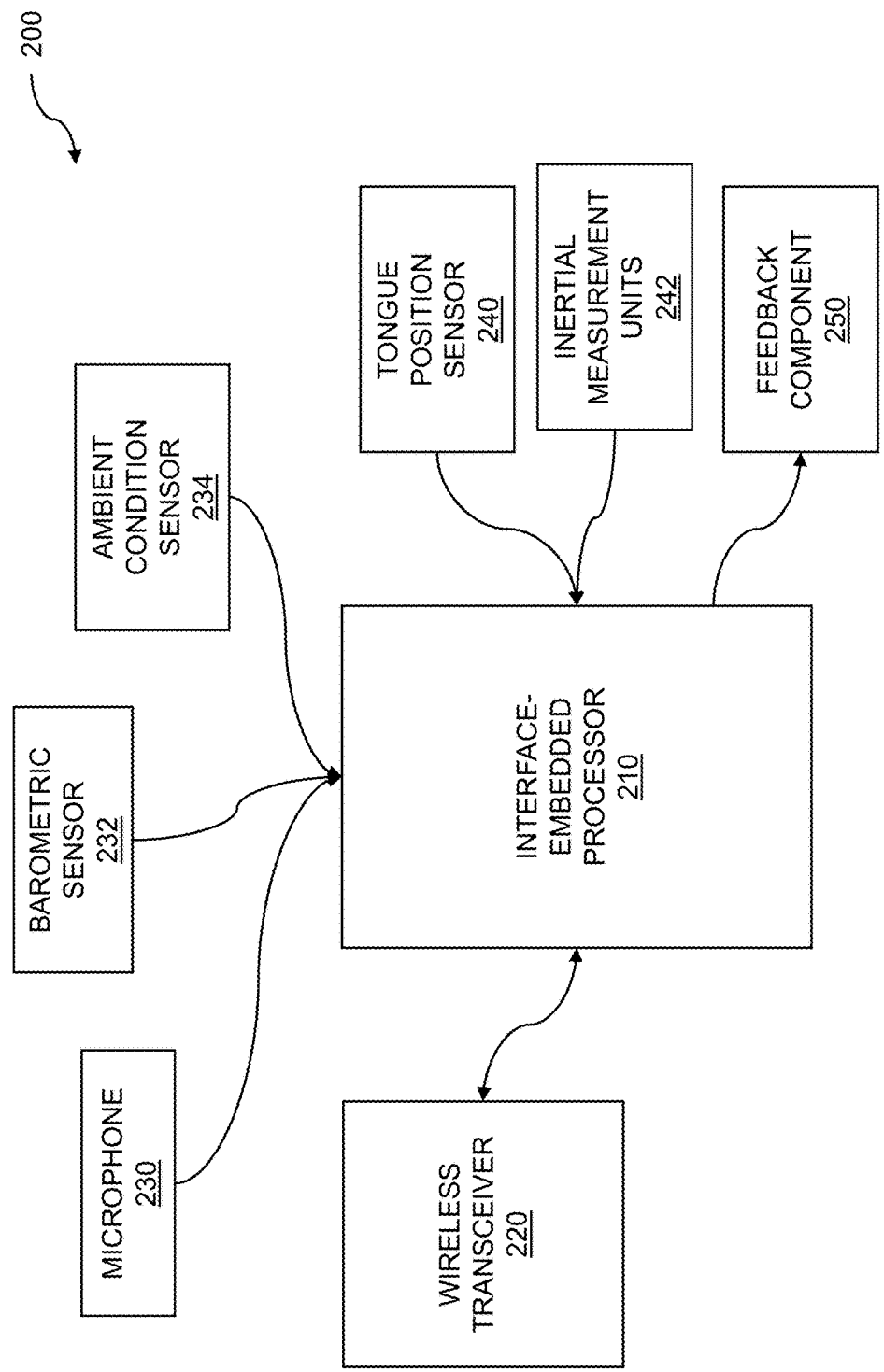
FIG. 2 is a system block diagram for remote augmented sensing.

FIG. 2 is a system block diagram for remote augmented sensing. A tongue position sensor, inertial measurement units, biometric sensors, and so on, can be used to collect data from and process data for a user. The data collecting and processing enables data manipulation using intraoral, connected devices. Wired connectivity is provided between a first device and a second device, both inside the mouth. The first device comprises a processor or a processing device. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth. Wireless connectivity is provided between the first device and a device outside the mouth. The wireless connectivity is enabled using a wireless transceiver. Data transmission is enabled between the first device and the device outside the mouth. The enabling includes powering at least the first device using an intraoral energy source.

A system block diagram for remote augmented sensing is shown 200. The system block diagram can include an interface-embedded processor 210, which can comprise the first device, as described throughout. The interface-embedded processor can process data collected from a variety of sensors. Embodiments can include coupling an interface-embedded preprocessor among the wireless transmitting device, the output from the TPS, and the at least two IMUs. The preprocessor can be used to calibrate, filter, convert, or otherwise handle data collected from the TPS and the IMUs. In embodiments, the preprocessing capabilities can be included in the interface-embedded processor. The system block diagram can include a wireless transceiver 220. The wireless transceiver can include a transmitter/receiver pair (TX/RX), where the wireless transceiver can transfer data between the interface-embedded processor and an external device. The external device can include a computer or processor, a smart device such as a smartphone or smart watch, a tablet computer, a laptop computer, and the like.

The system block diagram can include a variety of sensors that can be coupled to the interface-embedded processor. In embodiments, a microphone 230 can be coupled to the interface-embedded processor. The microphone can include an audio microphone, a transducer, or some other audio pickup device suitable for audio collection. The microphone can be operated normally on, normally off, etc. In embodiments, the microphone can be enabled based on the output from the TPS or the at least two IMUs. The microphone can capture audio data, speech data, and so on. In embodiments, the microphone can enable near-silent speech recognition. A barometric sensor 232 can be coupled to the interface-embedded processor. The barometric sensor can be used to determine barometric pressure with the oral cavity of the user. In embodiments, the barometric sensor can detect a tri-value state of air pressure within an oral cavity containing the interface. The tri-value state of air pressure can include nominal or ambient pressure, increased pressure, and decreased pressure. In embodiments, the tri-value state can include ambient barometric pressure, increased barometric pressure due to exhaling into a closed oral cavity, and decreased barometric pressure due to inhaling from a closed oral cavity. An ambient condition sensor 234 can be coupled to the interface-embedded processor. The ambient condition sensors can include biometric sensors. In embodiments, the biometric sensors can include temperature, heart rate, hydration, pH, oxygen, microbe, hormone, enzyme, blood pressure, jaw clenching force, and airflow sensors.

Further sensors can be coupled to the interface-embedded processor. In embodiments, a tongue position sensor (TPS) 240 can be coupled to the interface-embedded processor. The TPS can be used as a tongue-based gesture interface. The TPS can detect tongue position, tongue pressure, etc. Inertial measurement units (IMUs) 242 can be coupled to the interface-embedded processor. In embodiments, at least two IMUs can be coupled. The IMUs can be used to measure jaw position, acceleration, rotation, etc. In embodiments, the TPS and the at least two IMUs can be used to accommodate situational impairment experienced by a person. Situational impairments can include high or low volume noise, poor lighting, social constraints, and so on. Situational impairments can prevent a user from reading a display, interacting with a device such as a computing device, etc. A feedback component 250 can be coupled to the interface-embedded processor. The feedback component can provide haptic feedback, audio feedback, and so on. In embodiments, the feedback can originate in the processor and can be transmitted to the interface using the wireless connectivity. The feedback can be provided based on a range of actions, to accomplish a variety of tasks, etc. In embodiments, the feedback can be responsive to active oral manipulation by a user of the interface, passive monitoring of a user of the interface, and the like.

Figure 3:
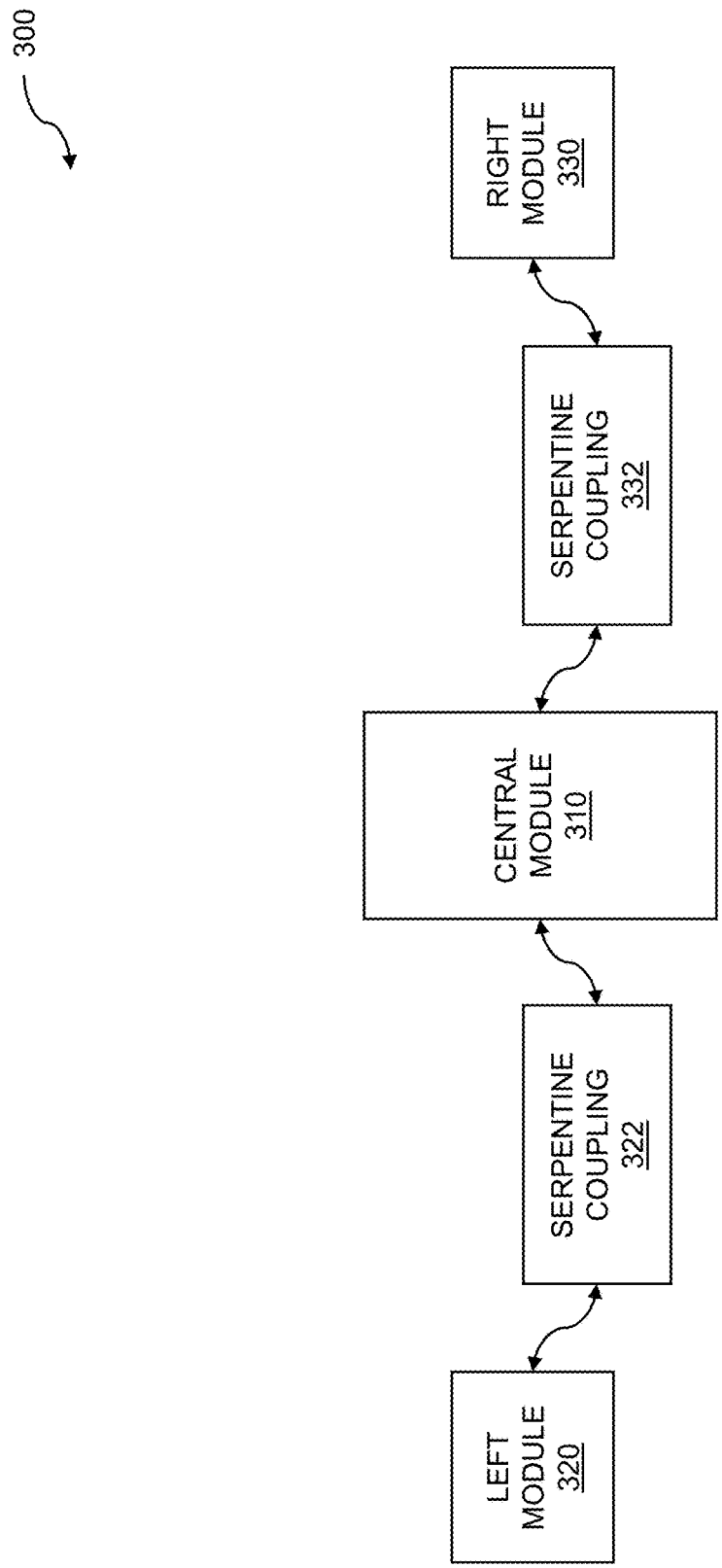
FIG. 3 is a system block diagram with devices and serpentine couplings.

FIG. 3 is a system block diagram with devices and serpentine couplings. Discussed throughout, two or more devices can communicate using one or more serpentine couplings. The use of the serpentine coupling between and among processors, sensors, transmitters, batteries, chargers, and other components, enables intraoral, connected devices. Wired connectivity is provided between a first device and a second device, both inside the mouth. The first device comprises a processor device. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth. Wireless connectivity is provided between the first device and a device outside the mouth. The wireless connectivity is enabled using a wireless transceiver. Data transmission is enabled between the first device and the device outside the mouth. The enabling includes powering at least the first device using an intraoral energy source.

The system block diagram 300 includes a central module 310. The central module can include a processor such as an interface-embedded processor or other such processing device. The interface-embedded processor can process data collected from a variety of sensors. Embodiments can include coupling an interface-embedded preprocessor between a wireless transmitting device and an output from a tongue position sensor (TPS). A preprocessor, which can also be associated with the central module, can be used to calibrate, filter, convert, or otherwise handle data collected from the TPS and the IMUs. In embodiments, the preprocessing capabilities can be included in the interface-embedded processor. The block diagram 300 can include a left module 320. The left module can include a device, where the device can include an IMU, a sensor, a smart sensor, and so on. The left module 320 can communicate with the central module 310 through a serpentine coupling 322. The serpentine coupling can comprise a serpentine wire, where the path of the serpentine wire jogs side to side along the length of the serpentine wire. The jogs, excursions, or "waves" of the serpentine wire can vary in amplitude such as a greater excursion (higher amplitude) or a lesser excursion (lower amplitude). The serpentine wire can have a varying serpentine period. The serpentine wire can include more waves more per unit length (shorter period) or fewer waves per unit length (longer period). The system block diagram 300 can include a right module 330. The right module can include another sensor, a wireless transceiver, another processing device, and so on. The right module 330 can communicate with the central module 310 through a second serpentine coupling 332. The second serpentine coupling 332 can be substantially similar to the first serpentine coupling 322 with respect to length, amplitude, or period, or can be substantially different from the first serpentine coupling with respect to one or more of length, amplitude, or period. The second serpentine coupling can comprise a different material composition and/or electrical makeup from the first serpentine coupling.

Figure 4:
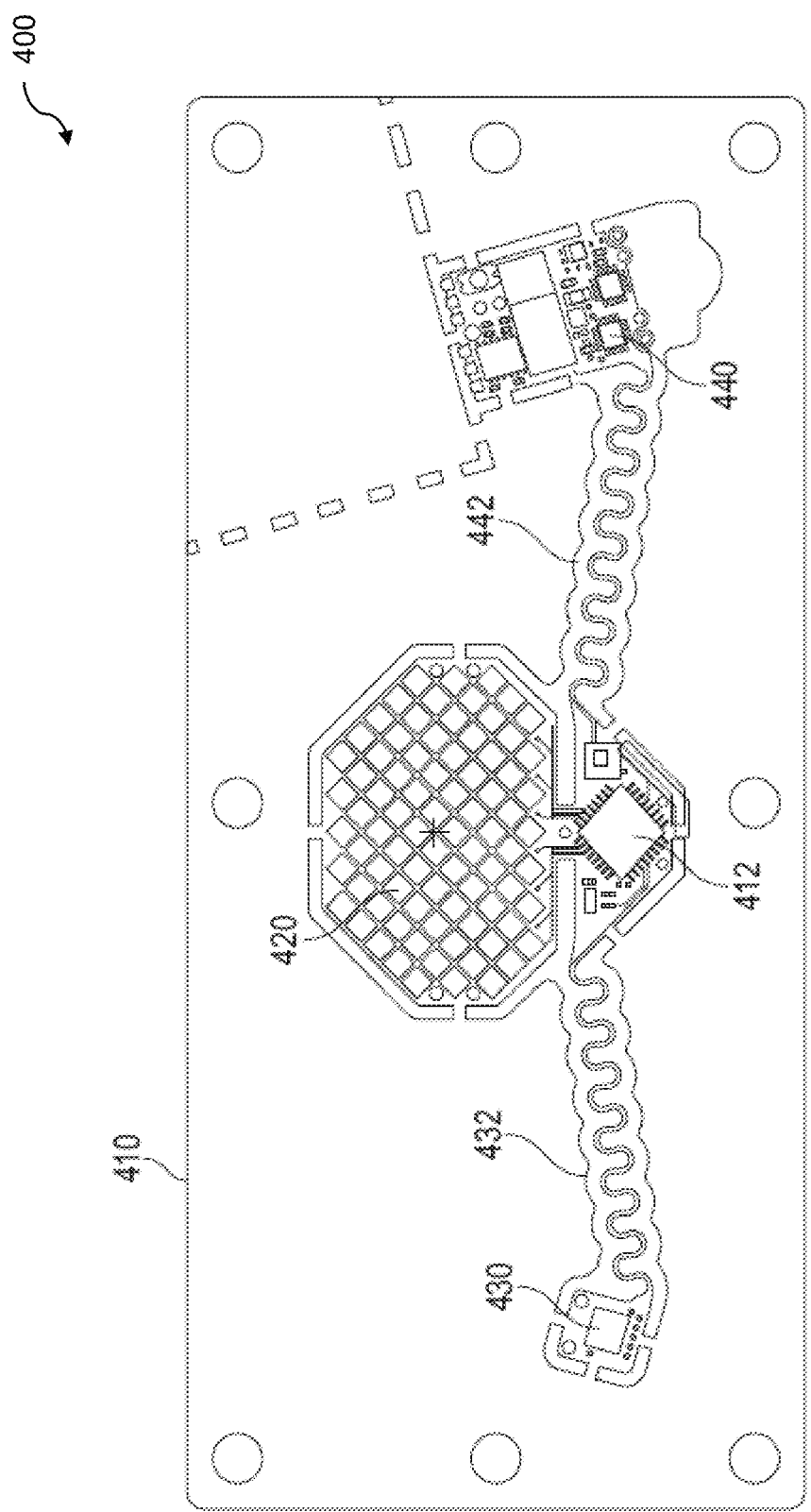
FIG. 4 illustrates a flexible circuit board with serpentine couplings.

FIG. 4 illustrates a flexible circuit board with serpentine couplings 400. Processing devices, sensors, interconnections, wireless transmitters, and so on, can be mounted onto or built into the flexible circuit board. The flexible circuit board can be applied to or placed into an intraoral device such as a retainer. The interconnections, which include serpentine couplings, support transmission of data between processing devices. The flexible circuit board with serpentine couplings enables intraoral, connected devices. Wired connectivity is provided between a first device and a second device, both inside the mouth. The first device comprises a processor device. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth.

A flexible circuit board 410 is shown. The flexible circuit board can include one or more insulating layers, one or more conducting layers, one or more ground plane layers, and so on. The flexible circuit board can comprise a material which is stable and safe for use for an intraoral application. The flexible circuit board can include mounting points for processing devices, sensors, and the like. The flexible circuit board can include mounting points for a first device, such as a device mounting 412. The device mounting 412 can support various device types, such as processing devices, transceiver devices, and the like. The device to be mounted in device mounting 412 can be the first device, as described throughout. The flexible circuit board can include a mounting point for a sensing device such as a tongue position sensor (TPS) 420. The flexible circuit board can provide further mounting points for devices, such as mounting points 430 and 440, connected by serpentine couplings 432 and 442. The additional devices can include sensors such as inertial measurement unit (IMU) sensors. The flexible circuit board can enable transmitting data between or among the processing devices. In embodiments, the transmitting data is accomplished through a serpentine coupling. The serpentine coupling can comprise a serpentine wire, where the serpentine wire can have a varying serpentine amplitude, a varying serpentine period, and so on. For the flexible circuit board 410, a first serpentine coupling 432 can couple a device at mounting point 430 to a device at mounting point 412. A second serpentine coupling 442 can couple a device at mounting point 440 to a device at mounting point 412. For the case of a pluggable serpentine coupling, the mounting points can be used for plug attachment to the serpentine coupling.

Figure 5:
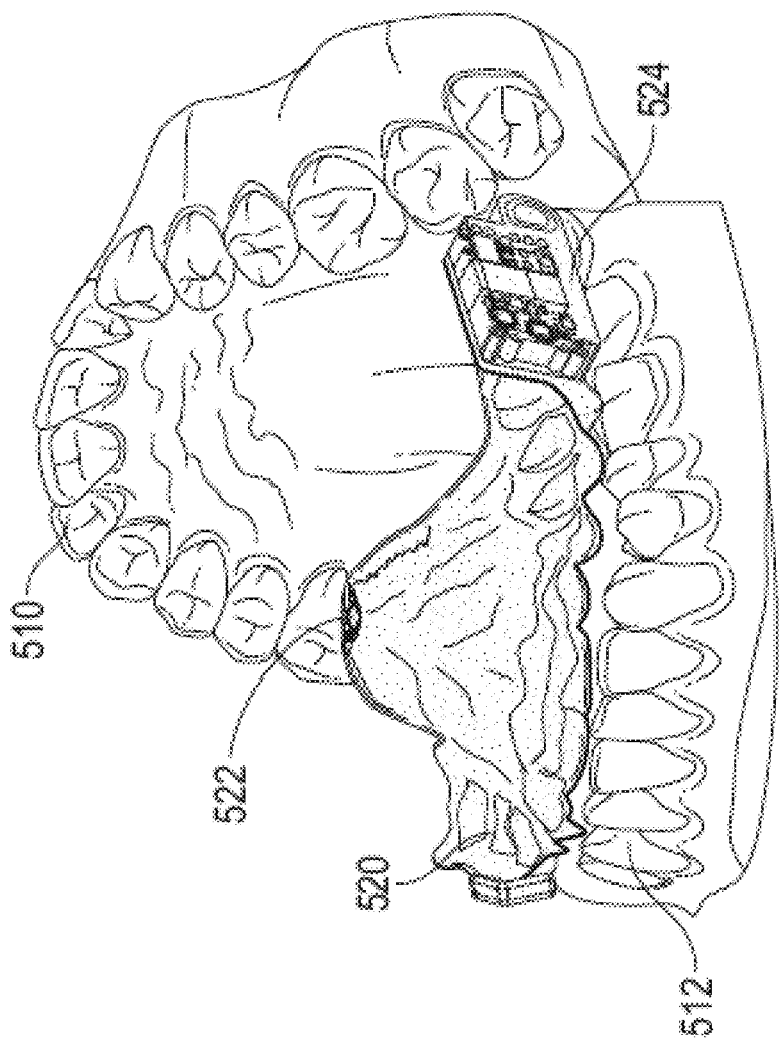
FIG. 5 shows a flexible circuit board and retainer in situ.

FIG. 5 shows a flexible circuit board and retainer in situ 500. An intraoral device can be used to provide oral function detection such as oral mouse function detection. The intraoral device can include a flexible circuit board, processing devices, sensor devices, communicating devices, and so on. The intraoral device can comprise a wearable prosthetic device such as a retainer or "bite plate." The oral functions that can be detected can include oral mouse functions. In embodiments, the oral mouse function detection includes mouse movement, mouse swipes, mouse clicks, mouse double-clicks, mouse wheel control, and so on. The flexible circuit board and retainer enable intraoral, connected devices. Wired connectivity is provided between a first device and a second device, both inside the mouth. The first device comprises a processor device. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth. Wireless connectivity is provided between the first device and a device outside the mouth. The wireless connectivity is enabled using a wireless transceiver. Data transmission is enabled between the first device and the device outside the mouth. The enabling includes powering at least the first device using an intraoral energy source.

Sensors, inertial measurement units, tongue gesture interfaces, and so on, can be coupled to a device such as a retainer. The retainer can be used by placing the retainer into an oral cavity of the user. A simulated oral cavity is shown, including upper teeth 510 and lower teeth 512. The retainer can detect tongue pressure, tongue movement, head movement, and so on. Discussed throughout, a tongue pressure sensor, two or more inertial measurement units, and other sensors can be coupled to a device that can be placed into an oral cavity of a user. In embodiments, the device can include a retainer 520. The retainer can include a customized retainer, where the customized retainer is fitted to a particular user to ensure proper fit and to enable comfort of the user. A tongue position sensor (TPS) 522 (partially obscured) can be coupled to the retainer. While in the example the TPS is shown place above the tongue, in embodiments, the TPS can be placed below the tongue. The TPS can detect tongue gestures such as tongue pressure, tongue position, tongue movement, and so on. Other sensors can be coupled to the retainer. In embodiments, at least two inertial measurement units (IMUs) are coupled to the wireless transmitting device. The wireless transmitting device can be collocated 524 with an IMU, a battery, a battery charging component, and so on. A further IMU or other sensor can be placed on the far side of the retainer from 524 or at another location (not shown).

Various types of sensors, including remote sensors, are used to capture data that includes barometric data, speech data, ambient condition data, and so on. Further collected data includes tongue position sensor (TPS) data, and data collected from the at least two inertial measurement units (IMUs). The collected data can be manipulated by a processor, where the data manipulation uses intraoral, connected devices. The sensors can include a microphone and a barometric sensor. The microphone can be used to collect audio data, speech data, and so on. The microphone can include an audio microphone, a transducer, or another component suitable for providing audio data to a data manipulation system. In embodiments, the microphone enables near-silent speech recognition. The output of the microphone can include an audio signal, where the audio signal can include an analog signal, a digital signal, etc. The microphone can include one or more usage states, where the usage states can include inactive, monitoring, etc. The microphone can be operated based on actions of a user of the microphone. In embodiments, the action of the microphone can be preprogrammed.

The barometric sensor can be used to detect changes in barometric pressure within an oral cavity. The barometric sensor can include a solid-state sensor, a micro-electromechanical system (MEMS), and so on. The output of the barometric sensor can include a signal value, code, etc. that can describe a tri-value state. In embodiments, the barometric sensor can detect a tri-value state of air pressure within an oral cavity containing the interface. The states can be represented by a value, a code, etc. In embodiments, the tri-value state can include ambient barometric pressure, increased barometric pressure due to exhaling into a closed oral cavity, and decreased barometric pressure due to inhaling from a closed oral cavity. Other sensors that can be used can include ambient sensors. An ambient conditions sensor can be used to measure and collect ambient conditions data associated with a person, such as ambient conditions within the oral cavity, biometric data, and so on. The output of the ambient condition sensor can include changes in biometric data. As with other sensors, the ambient sensor can include states, where the states can be associated with one or more biometric parameters. The biometric parameters can include absolute values, relative values, ranges, etc. In embodiments, the biometric sensors that are used can include temperature, heart rate, hydration, pH, oxygen, microbe, hormone, enzyme, blood pressure, jaw clenching force, and airflow sensors.

Figure 6:
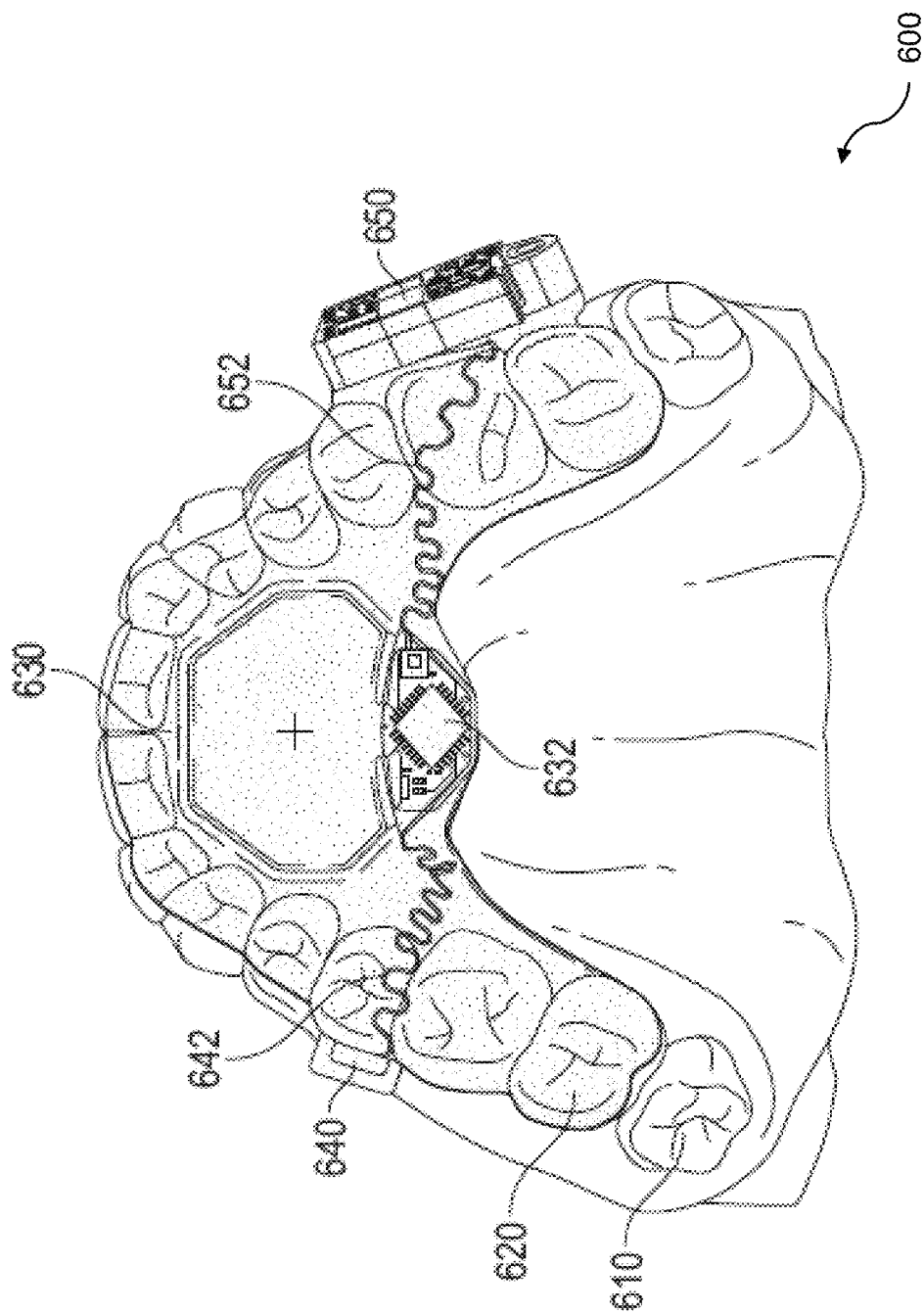
FIG. 6 illustrates modules interconnected by serpentine couplings.

FIG. 6 illustrates modules interconnected by serpentine couplings 600. As discussed above and throughout, an intraoral device can be used to provide oral function detection. The intraoral device can comprise a wearable or prosthetic device such as retainer, where the retainer can include a flexible circuit board, processing devices, sensor devices, communicating devices, data transmission devices, and so on. The oral functions that can be detected by the intraoral device can include oral mouse functions. In embodiments, the oral mouse function detection includes common mouse functions such as mouse movement, mouse swipes, mouse clicks, mouse double-clicks, mouse wheel control, and so on. The flexible circuit board and retainer support intraoral, connected devices. Wired connectivity is provided between a first device and a second device, both inside the mouth. The first device comprises a processor device. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth.

The upper half of a simulated oral cavity 610 is shown. Smart sensors, IMUs, a TPS, and so on, can be coupled to a device such as a retainer 620. The retainer can be used by placing the retainer into an oral cavity and over the teeth of the user. The retainer can detect tongue pressure, tongue movement, head movement, exhales, inhales, puffs, and so on. Discussed throughout, a tongue pressure sensor, two or more inertial measurement units, and other sensors can be coupled to a device that can be placed into an oral cavity of a user. Further, a wireless transmitter, a battery, and a battery charging component can be collocated with an IMU. The wireless transmitter can include a low-power Bluetooth transceiver. The battery charging component can include an inductive charging component such as a QI™ charging component. In embodiments, the device can include a custom retainer or other retainer. A tongue position sensor (TPS) 630 can be coupled to a processing device 632. As noted previously, while in the example the TPS is shown place above the tongue, in other embodiments, the TPS can be placed below the tongue. The TPS can detect tongue gestures such as tongue pressure, tongue position, tongue movement, and so on. Other sensors can be coupled to the retainer. In embodiments, at least two inertial measurement units (IMUs) such as IMUs 640 and 650 are coupled the processing device 632 using serpentine couplings 642 and 652. The serpentine couplings, which can include serpentine wire, can be placed between teeth, behind a last molar, over one or more teeth, and so on. Recall that the amplitude and the period of the serpentine wire can each vary. The wireless transmitting device can be collocated with an IMU 650, a battery, a battery charging component, and so on.

Figure 7:
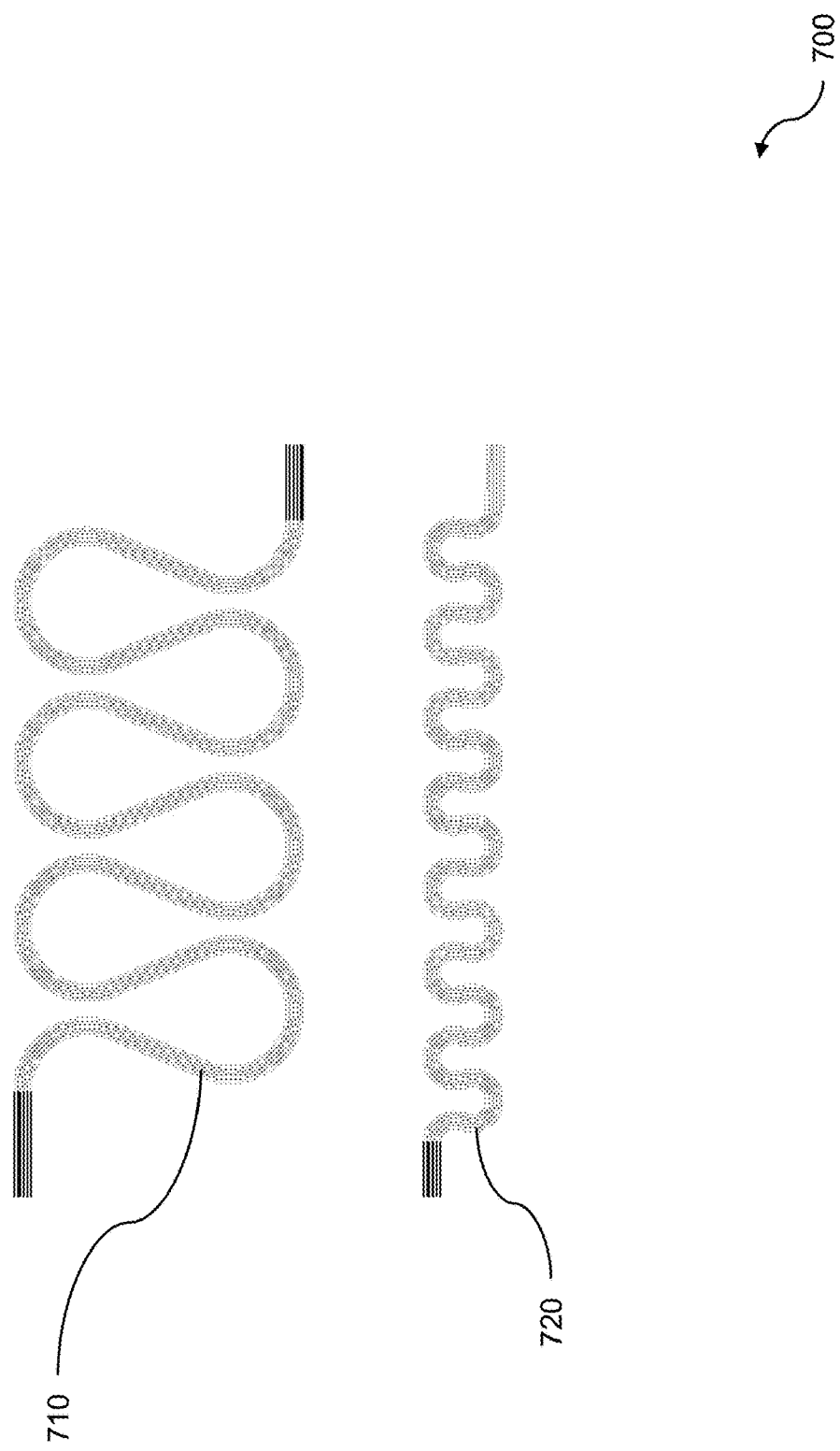
FIG. 7 illustrates serpentine coupling shapes.

FIG. 7 illustrates serpentine coupling shapes. Various serpentine coupling shapes enable intraoral, connected devices. Wired connectivity is provided between a first device and a second device, both inside the mouth. The first device comprises a processor device. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth. In the illustration 700, two serpentine coupling shapes are shown, serpentine 710 and serpentine 720. Other serpentine shapes are possible. The serpentine shape chosen for embedding inside a mouth, in, through, or over an intraoral interface, such as the retainers shown above, can enable three-dimensional routing of the serpentine coupling, including rises, falls, twists, bends, overlaps, swirls, rotations, and the like. The serpentine coupling can comprise an electrical cable. The serpentine coupling can enable three-dimensional overlap of the electrical cable within the mouth. The three-dimensional overlap can provide a conformal routing over a surface of the mouth. The electrical cable can have two or more conductors. The electrical cable can be a two-wire bus interface. The two-wire bus interface can be an I²C-Bus™ interface.

Various lengths and shapes of serpentine couplings can be predesigned and manufactured for intraoral use. To facilitate the widely varying shapes, sizes, and topologies of different mouths, the serpentine coupling can be pluggable on at least one end of the coupling. The pluggable couplings can enable flexible and ubiquitous coverage of many different mouths. In embodiments, the providing wired connectivity is accomplished by selecting a pluggable serpentine coupling from a predefined catalog of couplings. In embodiments, the predefined catalog of couplings includes serpentine couplings of various lengths, frequencies, or amplitudes. In embodiments, the selecting is based on a contour analysis of the inside of the mouth.

Figure 8:
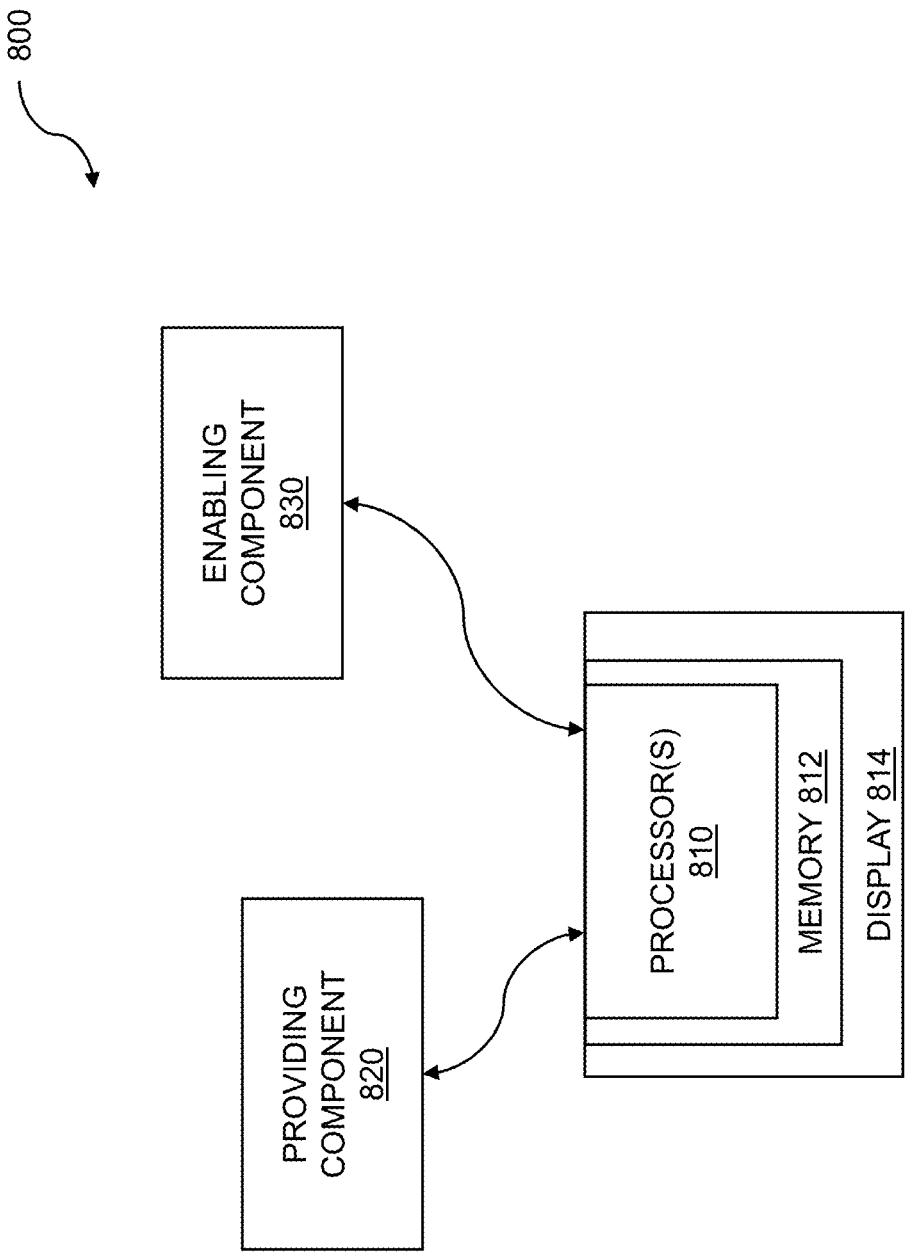
FIG. 8 is a system diagram for data manipulation.

FIG. 8 is a system diagram for data manipulation. Intraoral, connected devices can be used for data manipulation. The intraoral, connected devices can include processors, sensors, smart sensors, and so on, which can be used for remote sensing and other applications. The sensors can include "remote" sensors within a user's mouth, sensors adjacent to the user, and so on. In embodiments, the remote sensing can be accomplished using a barometric sensor, an ambient condition sensor, a microphone, inertial measurement units (IMUs), and so on. The sensors can be used to measure or detect a tri-value state of pressure within an oral cavity, speech including near silent speech, ambient conditions, etc. Data manipulation can further be accomplished using a prosthetic such as a retainer, where the retainer can be used to measure tongue position, pressure, and the like. The sensing, which can include augmented sensing, can be used as a hands-free input and output device for data manipulation, where hands-free operation can be used by people who may not be able to use other data manipulation devices such as keyboards, mice, trackpads, etc. The augmented sensing can be used for silent, covert, or discrete data manipulation. Data is transmitted between a first device inside a mouth and a second device within the mouth, where the data transmission is accomplished through a serpentine coupling or connection. Wireless connectivity between the first processing device and a device outside the mouth is provided using a wireless transmitting device. The system 800 can include one or more processors 810 and a memory 812 which stores instructions. The memory 812 is coupled to the one or more processors 810, wherein the one or more processors 810 can execute instructions stored in the memory 812. The memory 812 can be used for storing instructions, runtime libraries, data manipulation routines, sensor drivers, error codes or handling routines, and so on. The memory can further be used for storing sensor calibration data. Information such as sensor data can be shown on a display 814 connected to the one or more processors 810. The display can comprise a television monitor, a projector, a computer monitor (including a laptop screen, a tablet screen, a netbook screen, and the like), a smartphone display, a mobile device, or another electronic display.

The system 800 can include a providing component 820. The providing component 820 can be used to provide both wired connections intraorally and wireless connections extraorally. The wired connections that are provided enable connectivity between a first device and a second device, both inside the mouth. The wired connectivity is provided by a serpentine coupling. The serpentine coupling enables three-dimensional flexibility inside the mouth for the coupling. The serpentine coupling comprises an electrical cable. The serpentine coupling can be routed in the valley space between teeth, routed behind a last molar tooth, or routed over one or more teeth inside the mouth. The wireless connections that are provided can enable wireless connectivity between the first device and a device outside the mouth. The wireless connectivity can be enabled using a wireless transceiver. Data transmission is enabled between the first device and the device outside the mouth. The serpentine wire can include various shapes which can emulate the shape of a serpent, or essentially an "S" shape or side-to-side pattern. The "S" shape can include rounded waves such as sine waves, flat-topped waves such as square waves, and so on. In embodiments, the serpentine wire can have a varying serpentine amplitude, where the sizes, heights, or excursion of the serpentine wire can vary over the length of the serpentine wire. In other embodiments, the serpentine wire can have a varying serpentine period. The varying period can enable more or fewer "waves" along the length of the serpentine wire. The serpentine wire can comprise a bus for implementing a wired interface protocol, such as a two-wire bus interface, for example, an I²C-Bus™ interface.

The system 800 can include an enabling component 830. The enabling component 830 can be used for enabling data transmission between the first device and a device outside the mouth using a wireless transmitting device. The device outside the mouth can include a computer such as a laptop or desktop computer, a smartphone, a PDA, a tablet, and so on. The wireless connectivity can be based on wireless communications standards and techniques such as 802.11 Wi-Fi™, Bluetooth™, near field communication (NFC), near field magnetic induction (NFMI), ZigBee™, a wireless personal area network (WPAN), and so on. The wireless connectivity can include bidirectional communications capabilities. In embodiments, the wireless transmitting device is embedded in an oral sensing interface. The oral sensing interface can include a prosthetic device such as a retainer. The retainer can include sensors, contacts, communications components, and the like.

The system 800 can implement a computer system for data manipulation comprising: a memory which stores instructions; one or more processors coupled to the memory wherein the one or more processors, when executing the instructions which are stored, are configured to: provide wired connectivity between a first device inside a mouth and a second device inside the mouth, wherein the wired connectivity is provided by a serpentine coupling, and wherein the serpentine coupling enables three-dimensional flexibility inside the mouth for the coupling; provide wireless connectivity between the first device and a device outside the mouth, wherein the wireless connectivity is enabled using a wireless transceiver; and enable data transmission between the first device and the device outside the mouth.

Disclosed embodiments can include a computer program product embodied in a non-transitory computer readable medium for data manipulation, the computer program product comprising code which causes one or more processors to perform operations of: providing wired connectivity between a first device inside a mouth and a second device inside the mouth, wherein the wired connectivity is provided by a serpentine coupling, and wherein the serpentine coupling enables three-dimensional flexibility inside the mouth for the coupling; providing wireless connectivity between the first device and a device outside the mouth, wherein the wireless connectivity is enabled using a wireless transceiver; and enabling data transmission between the first device and the device outside the mouth.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general-purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are limited neither to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A processor-implemented method for data manipulation comprising:
    providing wired connectivity between a first device inside a mouth and a second device inside the mouth, wherein the wired connectivity is provided by a serpentine coupling, wherein the serpentine coupling is pluggable on at least one end of the coupling using a small form-factor plug, wherein the plug is configured and disposed to mate with a receptacle to complete an electrical connection, and wherein the serpentine coupling enables three-dimensional flexibility inside the mouth for the coupling;
    providing wireless connectivity between the first device and a device outside the mouth, wherein the wireless connectivity is enabled using a wireless transceiver; and
    enabling data transmission between the first device and the device outside the mouth.

2. The method of claim 1 wherein the enabling includes powering at least the first device using an intraoral energy source.

3. The method of claim 2 wherein the intraoral energy source comprises a battery, a capacitor, or an inductive field device.

4. The method of claim 1 wherein the serpentine coupling comprises an electrical cable.

5. The method of claim 4 wherein the serpentine coupling enables three-dimensional overlap of the electrical cable within the mouth.

6. The method of claim 5 wherein the three-dimensional overlap provides conformal routing over a surface of the mouth.

7. The method of claim 4 wherein the electrical cable has two or more conductors.

8. The method of claim 4 wherein the electrical cable comprises a two-wire bus interface.

9. The method of claim 8 wherein the two-wire bus interface comprises an I²C-Bus™ interface.

10. The method of claim 1 wherein the providing wired connectivity is accomplished by selecting a pluggable serpentine coupling from a predefined catalog of couplings.

11. The method of claim 10 wherein the predefined catalog of couplings includes serpentine couplings of various lengths, frequencies, or amplitudes.

12. The method of claim 10 wherein the selecting is based on a contour analysis of the inside of the mouth.

13. The method of claim 1 wherein the serpentine coupling is routed in the valley space between teeth of the mouth.

14. The method of claim 1 wherein the serpentine coupling is routed behind a last molar tooth of the mouth.

15. The method of claim 1 wherein the serpentine coupling is routed over one or more teeth inside the mouth.

16. The method of claim 1 wherein the first device comprises a processor device.

17. The method of claim 1 wherein the second device comprises an intraoral sensing device.

18. The method of claim 1 further comprising providing additional wired connectivity between the first device and a third device inside the mouth.

19. The method of claim 18 wherein the additional wired connectivity is provided by an additional serpentine coupling.

20. The method of claim 1 wherein the wired connectivity, the wireless connectivity, and the data transmission enables data manipulation in the device outside the mouth.

21. The method of claim 1 wherein the wired connectivity enables data manipulation inside the mouth.

22. A computer program product embodied in a non-transitory computer readable medium for data manipulation, the computer program product comprising code which causes one or more processors to perform operations of:
  providing wired connectivity between a first device inside a mouth and a second device inside the mouth, wherein the wired connectivity is provided by a serpentine coupling, wherein the serpentine coupling is pluggable on at least one end of the coupling using a small form-factor plug, wherein the plug is configured and disposed to mate with a receptacle to complete an electrical connection, and wherein the serpentine coupling enables three-dimensional flexibility inside the mouth for the coupling;
  providing wireless connectivity between the first device and a device outside the mouth, wherein the wireless connectivity is enabled using a wireless transceiver; and
  enabling data transmission between the first device and the device outside the mouth.

23. A computer system for data manipulation comprising:
  a memory which stores instructions;
  one or more processors coupled to the memory wherein the one or more processors, when executing the instructions which are stored, are configured to:
    provide wired connectivity between a first device inside a mouth and a second device inside the mouth, wherein the wired connectivity is provided by a serpentine coupling, wherein the serpentine coupling is pluggable on at least one end of the coupling using a small form-factor plug, wherein the plug is configured and disposed to mate with a receptacle to complete an electrical connection, and wherein the serpentine coupling enables three-dimensional flexibility inside the mouth for the coupling;
    provide wireless connectivity between the first device and a device outside the mouth, wherein the wireless connectivity is enabled using a wireless transceiver; and
    enable data transmission between the first device and the device outside the mouth.

* * * * *